United States Patent [19]

Tirelli et al.

[11] Patent Number: 5,074,150

[45] Date of Patent: Dec. 24, 1991

[54] INSTRUMENT FOR THE MEASUREMENT OF THE CAVITATION OR EBULLITION RATE IN A LIQUID

[75] Inventors: Dino Tirelli; Pietro Gori, both of Bologna, Italy

[73] Assignee: Comitato Nazionale Per La Ricerca E Per Lo Sviluppo Dell'Energia Nucleare E Delle Energie Alternative, Italy

[21] Appl. No.: 380,100

[22] Filed: Jul. 14, 1989

[30] Foreign Application Priority Data

Jul. 15, 1988 [IT] Italy .............................. 48198 A/88

[51] Int. Cl.[5] .......................................... G01D 29/02
[52] U.S. Cl. .................................................... 73/590
[58] Field of Search ............ 73/590, 592, 1 DV, 19.03

[56] References Cited

U.S. PATENT DOCUMENTS

| | | | |
|---|---|---|---|
| 3,538,747 | 11/1970 | Munch | 73/53 |
| 3,548,640 | 12/1970 | Deason et al. | 73/590 |
| 4,058,004 | 11/1977 | Hammitt et al. | 73/86 |
| 4,445,206 | 4/1984 | Audenard | 73/1 DV |

*Primary Examiner*—John E. Chapman
*Attorney, Agent, or Firm*—Pollock, Vande Sande & Priddy

[57] ABSTRACT

An apparatus for the measurement of the cavitation or ebullition rate comprises an accelerometric transducer in contact with the liquid under cavitation or boiling and a filter and amplifier connected in cascade and having an input electrically connected to the transducer for providing on the output of the amplifier a signal containing information about cavitation or ebullition. This signal is then processed and displayed by two separate circuits. The first threshold circuit is connected to the output of the amplifier for eliminating signals having a value lower than a preset threshold value, a flash follower connected to the threshold circuit, and a counter and display connected to the flash follower. The display is adapted to provide a count of events in the signal sensed by the accelerometric transducer which surpass the preset threshold value. The second circuit includes an r.m.s. converter for providing the r.m.s. value of the signal obtained on the output of the amplifier. An integrator is connected to the converter for obaining at its output the average value of the r.m.s. value. Read-out circuit indicates the average value of the r.m.s.

5 Claims, 2 Drawing Sheets

INSTRUMENT FOR THE MEASUREMENT OF THE CAVITATION OR EBULLITION RATE IN A LIQUID

DESCRIPTION OF THE INVENTION

1. Field of the Invention

The invention relates to an instrument for the measurement of the cavitation or ebullition rate, two similar phenomena that occur in liquids subjected to predetermined physical conditions. The two phenomena even if different, develop substantially in the same way.

When a liquid mass is either heated under a constant pressure or when its pressure is reduced under a constant temperature, an extreme is reached in which cavities become visible and growing up, i.e. bubbles of vapor or gas and vapor. The growth of the bubble may be explosive if it is the result of vaporization in the cavity.

Subsequently, if the liquid mass is subjected to a decreasing temperature under a constant pressure, or to an increasing pressure under constant temperature, the bubble undergoes a volume reduction up to its collapse, and the collapse will be the more implosive with the decrease of the gas content, with respect to the vapor, that is contained in the cavity.

This phenomenon of growth and collapse of cavities is called undercooled ebullition when it is produced by a variation of temperature above or below with respect to the saturation value, while when it is obtained by a variation of the pressure below or above the saturation value it will be called cavitation.

Without entering further into the details of those phenomena it must be emphasized that the implosion process of a bubble goes through an initial phase in which the surrounding liquid, due to its inertia, acquires an increasing centripetal velocity, thus creating a geometrical instability such as to generate a very high speed microjet that destroys the cavity with a shock like the water-hammer.

The effects caused by cavitation and by ebullition can be divided into three groups:
  effects which modify the motion of the liquid;
  effects which cause an erosion of the solid surfaces contacting the liquid;
  effects which produce noise and vibration, either accompanied or not by the preceding effects.

For the sake of simplicity of disclosure, from now onwards both phenomena will be identified with the term. cavitation.

In the field of applied hydrodynamics, the cavitation effects are generally undesired because an uncontrolled cavitation can cause serious damages, if not catastrophic damages, and consequently the need for controlling or avoiding it imposes heavy constraints in the design and the use of hydraulic apparatus (turbines, pumps, valves, etc.). It should however be mentioned that some apparatus are designed just to utilize the phenomenon of cavitation, for instance cavitating jets for cleaning purposes or drilling boreholes.

In all other kinds of apparatus the cavitation reduces the performances of the apparatus and moreover produces erosions at the interior of the same, by removing material from the surfaces contacting the liquid in the areas where the implosion of the cavities occurs. Any kind of material is damaged (metals, rubber, plastics, glass, quartz and concrete).

Having illustrated the importance of the cavitation and the undesirable effects of the same, it should be clear that it will be advisable to have at disposal a simple and precise instrument for measuring its amount and to prevent the phenomenon if this is undesired.

As stated above, cavitation is normally an undesired phenomenon. Its occurrence in particular operating conditions of any general apparatus may not be easy to detect, indeed quite often in closed apparatus only the posteriori effect of cavitation may be detected by inspection, mainly because the typical noise of cavitation may be masked by other uncorrelated sources of noise or vibration usually present in mechanical apparatus handling fluids. The implosion noise caused by cavitation occurs in very short bursts of energy having a spectrum of characteristic frequency concentrated in a relatively narrow range with a short exponential decay (a. few cycles). In the jargon used in this field, these short energy bursts caused by cavitation are called "flashes", and this term will be used for convenience throughout the following disclosure. These "flashes" caused by cavitation have some characteristics by which, according to the invention, they may be identified as to their presence and occurrence even if immersed among other noise of other origin than cavitation, either periodic or non periodic, that is usually present in any kind of machinery.

SUMMARY OF THE INVENTION

It is therefore an object of the present invention to provide an instrument for the measurement of the rate of ebullition or cavitation comprising an accelerometer rigidly fastened to the vessel that contains the cavitating or boiling liquid to be kept under control; amplification and filtering means, electrically connected to the accelerometer, for processing the signal on the output of the accelerometer and to provide on its output a signal containing the information of interest (flashes caused by cavitation or boiling); discriminating means, electrically connected to said filtering and amplification means for isolating from said signal the information of interest (flashes not from cavitation or boiling); first display means, electrically connected to the discrimination means; means, connected to the filtering and amplification means, for obtaining from the output signal its r.m.s. value averaged in time and to provide on the output of the discrimination on means a signal indicating the r.m.s. value; second display means, electrically connected to the r.m.s. value, so that the second display means provide on the output the information relating to the power of the phenomenon; while the first display means provides the information about a possible mechanical noise source superposed to the phenomenon of interest (cavitation or boiling information).

It is a further object of the present invention an instrument for the measurement of the cavitation or ebullition rate, characterized in comprising: an accelerometer fastened to the vessel containing the liquid to be kept under control; filtering and amplification means connected to said accelerometer for processing the signal on the output of the latter and to provide at its output a signal containing the information of interest (flashes of cavitation or boiling); discriminating means, electrically connected with the filtering and amplification means for isolating from the signal the number of flashes in the unit of time; comparator means having two predetermined limit values; actuating means controlled by the comparator means, so that if the lower flash value limit set on the comparator is surpassed, the actuator signals an alarm, while if the higher value is surpassed, the actuator will shut off the apparatus.

BRIEF DESCRIPTION OF THE DRAWINGS

The invention will now be disclosed by way of example with reference to the attached drawings, wherein.

DESCRIPTION OF THE PREFERRED EMBODIMENT

Figure 1:
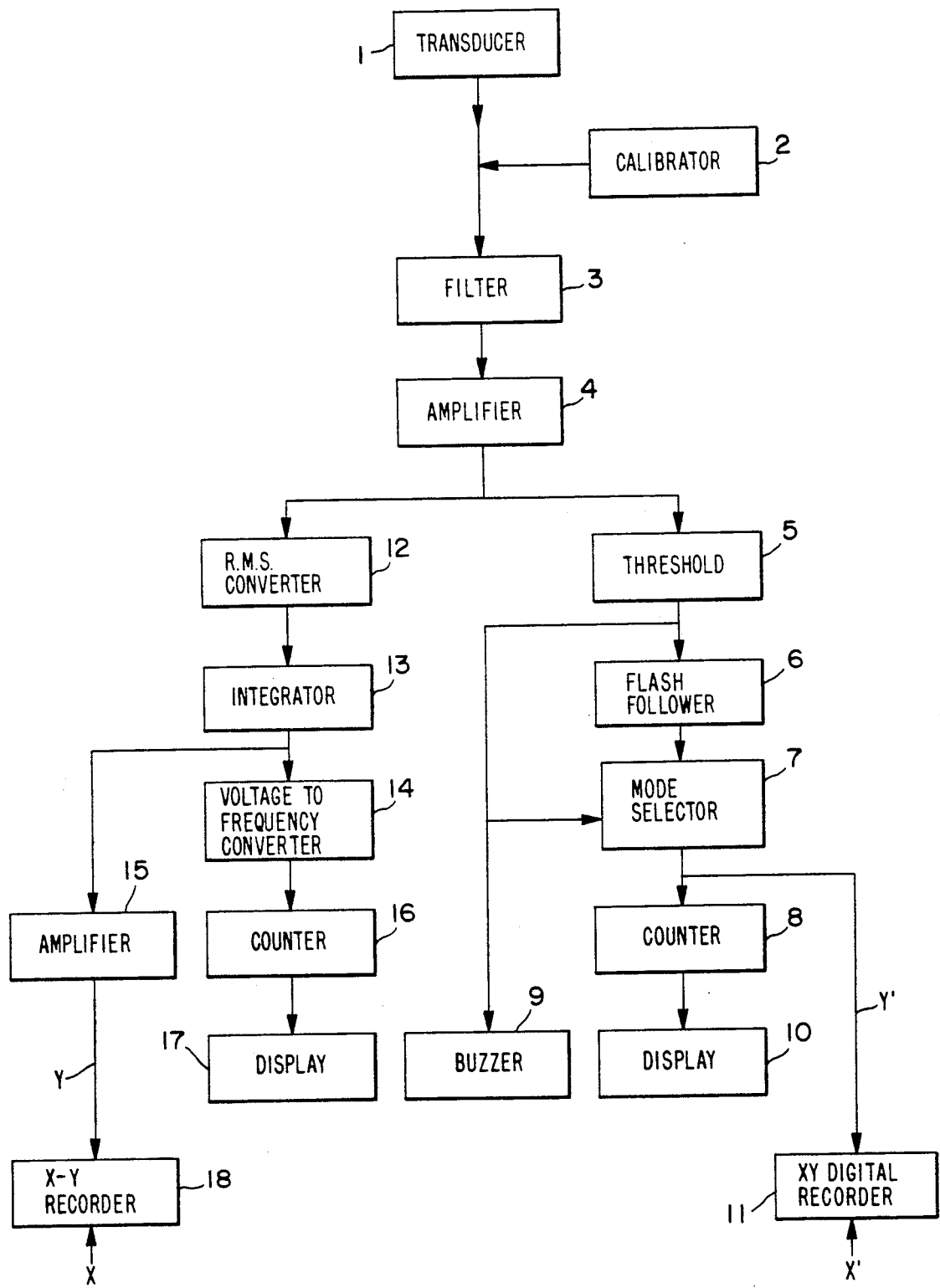
FIG. 1 is a block diagram of the measurement instrument of the present invention.

FIG. 1 shows, at a level of block diagram, the device according to the present invention. A preamplified accelerometric transducer 1 contained in a metal housing, is put in contact with the liquid under cavitation or boiling or is fastened to the external wall of the vessel containing it. In the preferred embodiment this transducer has a resonance frequency of 40 KHz with a high sensitivity at said frequency. The signal coming from the transducer 1 is sent to a passband filter 3 having a bandpass around the resonance frequency of the transducer 1 (in the preferred embodiment said bandpass goes from 35 to 50 KHz) for eliminating possible frequencies of mechanical or hydrodynamic origin which appear in the lower part of the frequency spectrum, and possible electrical discharges, transients and hydrodynamic perturbances appearing in the upper part of the frequency spectrum. This allows the utilization of the transducer in the area of maximum efficiency.

The output signal from the filter 3 is applied to a narrow bandpass amplifier to amplify it. As a matter of fact, the signal at the input of the amplifier comprises a series of very short trains of damped waves (flashes) created by the implosion shocks, having a variable amplitude and at the resonance frequency of the transducer, spaced one from the other by intervals practically ranging from zero when the phenomenon is appearing and tending towards infinity when the phenomenon is absent.

At this moment the signal on the output of the amplifier 4 follows two parallel paths, a first one of analog processing and the other one of digital processing. In the chain of analog processing, the signal is sent to a r.m.s. converter voltmeter 12 which provides the true r.m.s. value of the signal coming from the accelerometer at that application point. The output signal of block 12 representing the r.m.s. value is sent to the integrator circuit 13, having preferably a time constant ranging from 1 to 10 seconds, and subsequently it is sent to a voltage/frequency converter 14, which provides the output signal to a counter 16. The result of the counting is displayed by an indicator 17. Clearly, blocks 14, 16 and 17 could be replaced by a suitably calibrated digital voltmeter. It is furthermore possible to pick up the signal on the output from block 13, to amplify it by means of an amplifier 15 and to provide it from its output as a signal Y to an analog XY recorder 18, that will provide a graphic display of the phenomenon being studied. The other input, X, to the XY recorder can be a signal related for instance to the pressure or velocity of the fluid in the plant being monitored. This signal X can be derived in a known way from a pressure transducer not shown in the drawing. In this way the relationship cavitation/pressure can be plotted and kept under study or control.

The digital processing chain comprises a threshold circuit 5, having an adjustable level that can be preset with a suitable control, not shown. The threshold circuit 5 actually operates as a limit or amplitude discriminator for the measurement of the phenomenon, in the sense that all the signals having a value lower than the threshold will not be considered, while those having a higher value will be processed. The signal on the output of block 5 is supplied to a flash follower 6 and from this through a selector 7 to a counter 8. The "flash" follower 6, and the threshold circuit 5 cooperate in the sense that by means of the mode selector 7 it is possible to count the number of cycles contained within a "flash" or the number of "flashes". The selector 7 is provided with a control for selecting either mode of operation, i.e. counting of cycles in the "flashes" or counting of the number of flashes. The selector 7 is provided also with an auxiliary control that establishes the gate time that the operator chooses to select. In this way the counter 8 counts and displays by means of the indicator or display 10 the "flashes" or the number of cycles which have occurred within a predetermined time interval, and therefore their quantification.

The controls of the mode selector 7 and its internal structure have not been shown in detail since their structure and operation are considered obvious to a person skilled in electronic instrumentation.

The output signal from the block 5 is moreover picked up and branched on the selector 7 and on a beeper 9, that transforms the flashes into a signal in the acoustical range. It is furthermore possible to pick up the signal on the output from the selector 7 and to apply it as a signal Y' to a digital-input XY recorder for obtaining also in this case a graphic display of the phenomenon. The X' digital input to the digital-input XY recorder 11 is the same signal X applied to analog XY recorder 18 after having been converted into a digital signal by means of a conventional Analog-to-Digital converter (not shown). Between the transducer 1 and the filter 3 a calibrator 2 is inserted, which has the purpose of cooperating with the selector 7 for performing a calibration and for checking the resonance frequency of the crystal Actually, this calibrator provides a sinusoidal waveform at the resonance frequency of the transducer (in our case 40 KHz) to the chain and by means of the selector one can actually check the alignment. Conveniently the calibrator 2 may provide several levels of amplitude of the calibration sinewave as it is conventional for these accessories.

The instrument disclosed in FIG. 1 provides at the same time the indications about the phenomenon being examined in an analog and digital way. The analog indication, taking into account also the amplitudes, in addition to the duration, of the flashes, represents the power and in consequence the degree of erosivity of the phenomenon. The digital indication allows the recognition of a possible mechanical source superposed to the phenomenon being examined (a generator of mechanical shocks having a periodic behavior).

Figure 2:
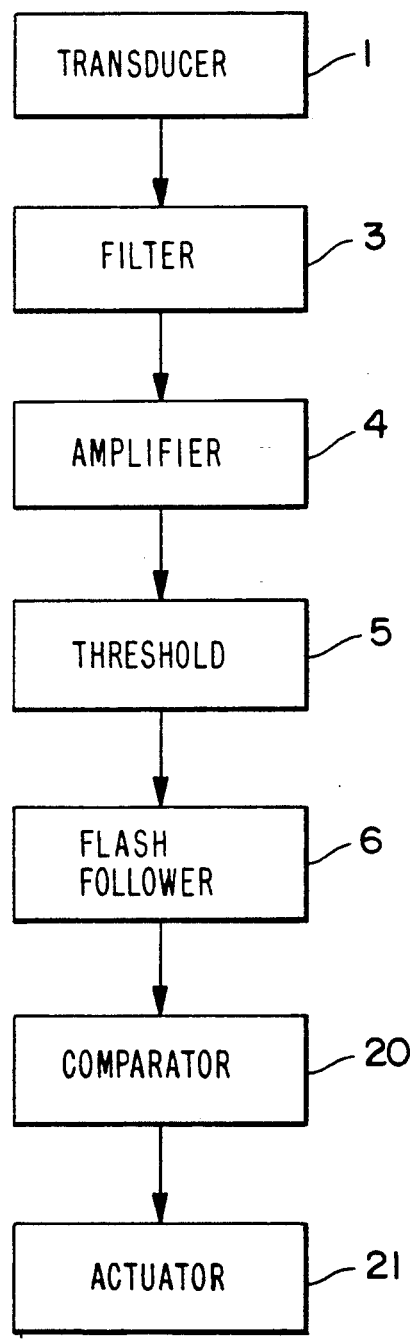
FIG. 2 is a block diagram of the measurement instrument of the present invention in a simplified form, suitable for signaling and preventing the phenomenon.

With reference to FIG. 2, now a further embodiment of the measurement instruments of the present invention will be disclosed, in a more simplified form, and suitable to be included in devices subjected to the risk of cavitation for signaling and preventing the phenomenon.

As it can be remarked, the block diagram of FIG. 2 follows a part of the digital processing chain of FIG. 1;

in particular, there are included the transducer 1, the filter 3, the amplifier 4, the threshold circuit 5 and the flash follower 6, that have been described with reference to FIG. 1. The flash follower circuit 6 provides its signal to a comparator 20 which is a comparator having two limit values. In the case that the lower value has been surpassed, the comparator 20 provides on its output an alarm signal, while if the higher value is surpassed the comparator 20 commands the actuator 21 to shut off the plant. This may be, for instance, very important in heating boilers, in which the appearance of cavitation or boiling must not occur, but where the boilers must actually work in conditions very close to the beginning of the phenomenon in order to reduce their dimensions and consequently their costs. A further application occurs in connection, for instance, with fuel elements of fast nuclear reactors, where clearly the importance of keeping the phenomenon under control is greater.

Clearly, for a person skilled in the art, further applications of the principle of the present invention are possible without departing from the scope of the invention itself.

We claim:

1. An apparatus for the measurement of the cavitation or ebullition rate in a liquid comprising:
    an accelerometric transducer in contact with means containing liquid under cavitation or boiling;
    filtering and amplifying means connected in cascade and having an input electrically connected to said accelerometric transducer for providing on the output of said amplifying means a signal containing information about cavitation or ebullition of said liquid, said signal including short bursts or flashes having periodic or non-periodic form;
    threshold means connected to the output of said amplifying means for eliminating signals having a value lower than a preset threshold value;
    a flash follower means having an input connected to the output of said threshold means;
    counter and display means connected to the output of said flash follower means, said counter and display means being adapted to provide a count of events in the signal sensed by said accelerometric transducer which surpass said preset threshold value of said threshold means;
    an r.m.s. converter also connected to the output of said amplifying means for providing the r.m.s. value of the signal obtained on the output of said amplifying means;
    integrator means connected to the output of said r.m.s. converter for obtaining at the output of said integrator the average value of said r.m.s. value;
    read-out means for providing indication of said average value of said r.m.s. and including a voltage-to-frequency converter, a counter and a display connected in cascade.

2. An apparatus according to claim 1, further comprising a mode selector connected between said flash follower means and said counter means for selecting a mode of operation, such that the signal supplied to said counter means relates either to the number of cycles in a flash or to the number of flashes.

3. An apparatus according to claim 2, wherein the output of said mode selector is connected to a first input of an XY recorder, to the other input of which is applied a preselected signal relating to a magnitude in function of which the signal applied to the first input has to be plotted.

4. An apparatus according to claim 1, wherein the output of said integrator is connected to an amplifier, the output of which is connected to a first input of an XY recorder, to the other input of which is applied a preselected signal relating to a magnitude in function of which the signal applied to the first input has to be plotted.

5. An apparatus according to claim 1, wherein said filtering and amplification means comprise a passband filter 35–50 KHz and a narrow band amplifier.

* * * * *